United States Patent [19]

Mixon et al.

[11] Patent Number: 5,069,907

[45] Date of Patent: Dec. 3, 1991

[54] SURGICAL DRAPE HAVING INCORPORATED THEREIN A BROAD SPECTRUM ANTIMICROBIAL AGENT

[75] Inventors: Grover C. Mixon, Kingstree, S.C.; Willard L. Morrison, Winston-Salem, N.C.

[73] Assignee: Phoenix Medical Technology, Andrews, S.C.

[21] Appl. No.: 498,193

[22] Filed: Mar. 23, 1990

[51] Int. Cl.⁵ .............................................. A61L 15/00
[52] U.S. Cl. .................................... 424/445; 424/402; 424/404; 523/111; 604/307; 128/849
[58] Field of Search ................... 424/402, 404, 78, 80, 424/445; 128/308; 523/111; 604/307

[56] References Cited

U.S. PATENT DOCUMENTS

| | | | |
|---|---|---|---|
| 4,181,786 | 1/1980 | Mune | 424/404 |
| 4,310,509 | 1/1982 | Burglund | 424/78 |
| 4,311,479 | 1/1982 | Fenn | 424/404 |
| 4,323,557 | 4/1982 | Rosso | 424/80 |
| 4,340,043 | 7/1982 | Seymour | 604/307 |
| 4,460,369 | 7/1984 | Seymour | 128/156 |
| 4,542,012 | 9/1985 | Dell | 424/28 |
| 4,584,192 | 4/1986 | Dell | 424/81 |
| 4,643,181 | 2/1987 | Brown | 424/445 |
| 4,675,347 | 6/1987 | Mochizuki et al. | 523/122 |
| 4,727,868 | 3/1988 | Szycher | 424/402 |
| 4,826,945 | 5/1989 | Cohn | 424/78 |
| 4,855,139 | 8/1989 | Srinivasan | 424/404 |

FOREIGN PATENT DOCUMENTS

| | | |
|---|---|---|
| 0251679 | 7/1988 | European Pat. Off. . |
| 00219673 | 3/1987 | Netherlands ............... 267/275 |

*Primary Examiner*—Thurman K. Page
*Assistant Examiner*—William E. Benston, Jr.
*Attorney, Agent, or Firm*—Thompson, Hine and Flory

[57] ABSTRACT

A surgical drape is disclosed. The drape comprises a synthetic polymeric film or fabric having incorporated therethrough an amount of an antimicrobial agent. The drape may optionally have an adhesive layer attached to one of its external surfaces wherein the adhesive layer has dispersed therethrough an antimicrobial agent. The preferred antimicrobial agent used is 5-chloro-2-(2,4-dichlorophenoxy)phenol.

5 Claims, No Drawings

SURGICAL DRAPE HAVING INCORPORATED THEREIN A BROAD SPECTRUM ANTIMICROBIAL AGENT

BACKGROUND OF THE INVENTION

1. Field of the Invention

The present invention relates to a polymeric sheet material having a broad spectrum antimicrobial agent incorporated therein. More particularly, the invention resides in a surgical drape having a broad spectrum antimicrobial agent incorporated in the polymeric material of the drape wherein the antimicrobial agent is released from the drape over a period of time when the drape is applied to the skin.

2. Brief Description of the Prior Art

Human skin is a source of contaminating organisms, since in addition to its normally innocuous bacterial flora, from time to time it may be colonized by pathogenic organisms. Experiments have suggested that pathogenic organisms do not usually survive on normal skin. Under most circumstances, the bacteria of normal skin flora cannot cause wound infection but in the presence of foreign materials, the pathogenic potential of these bacteria appears to be considerably enhanced. Furthermore, the likelihood of bacterial contamination is at a peak immediately preceding, during, and following surgical procedures. Accordingly, to prevent contamination, it is imperative that the skin be effectively disinfected before a surgical incision is made, and during the entire surgical procedure.

Several methods have been proposed to prevent infections associated with surgical incisions. The first method involves applying to the skin surface a topical bactericidally active or antimicrobial agent. These agents typically are in the form of preoperative skin preps, surgical scrub tissues, washes, wound cleaners, lotions and ointments. Although such topical applications are effective for shorter periods of times, their efficacy is limited as a result of their limited delivery time.

U.S. Pat. Nos. 4,542,012 and 4,584,192 propose the application of an antimicrobial agent by depositing a composition having an antimicrobial agent dispersed therein onto human skin and forming an antiseptic film on the skin. In these applications, the film-forming composition is applied to the skin as a liquid solution in a fugitive solvent. Upon contact, the solvent evaporates, leaving on the skin a thin film containing an antimicrobial agent.

Topical application of antimicrobial agents has also been accomplished by using surgical incise drapes which comprise an antimicrobial agent-containing pressure-sensitive layer as an adhesive. For example, U.S. Pat. Nos. 4,310,509 Berglund et al. and 4,323,557 to Russo et al. describe surgical incise drapes which comprise such an adhesive to provide continued asepsis. More specifically, U.S. Pat. No. 4,310,509 discloses a pressure-sensitive adhesive composition which contains chlorhexidene or a complex of polyvinylpyrrolidone and iodine which is applied onto a polymer sheet material, such as polyethylene or polyurethane, for use as a surgical drape. According to the reference, the drape is applied to the skin with the adhesive side contacting the skin so that the antimicrobial agent can be released from the adhesive to the wound prior to and during incision. U.S. Pat. No. 4,323,557 discloses a similar drape, wherein the pressure-sensitive adhesive comprises n-vinylpyrrolidone residues in the polymer backbone. Iodine is complexed with these residues.

U.S. Pat. Nos. 4,340,043 and 4,460,369 to Seymour disclose polymeric sheet materials having an adhesive layer, wherein an antimicrobial is disseminated throughout the adhesive layer. The antimicrobial is preferably a silver sulphadiazine. In use, the polymeric material is applied to the skin, adhesive side down.

Similarly, U.S. Pat. No. 4,643,181 to Brown discloses a surgical dressing or incise drape material containing a substrate coated with an antimicrobial containing adhesive. The antimicrobial is polyhexamethylene biguanide hydrochloride, and the dressing or drape is applied to the skin such that the adhesive directly contacts the skin.

U.S. Pat. No. 4,675,347 discloses an antimicrobial latex composition suitable for use in the manufacture of medical devices and the like, and in particular, urethral catheters. The composition is made from a cationic latex composition having incorporated therein a cationic antimicrobial agent. The references does not disclose the use of the latex as a surgical drape.

SUMMARY OF THE INVENTION

In accordance with the present invention, a sheet material for use as a surgical drape is provided which contains an antimicrobial agent dispersed therein. The surgical drape is capable of releasing the antimicrobial agent over a period of time and replenishing the antimicrobial agent to the surface of the drape as it is removed. The incorporation of the antimicrobial material in the drape enables protection to a patient against infections associated with surgery and to medical personnel working on the patient.

In accordance with one embodiment of the present invention, the surgical drape comprises a synthetic flexible polymeric film having incorporated therein an antiseptically effective amount of broad-spectrum antimicrobial agent. In a particularly preferred embodiment, the polymeric material is either polyethylene or polyurethane, and the antimicrobial agent is 5-chloro-2-(2,4-dichlorophenoxy)phenol.

In another embodiment, the present invention relates to a surgical drape comprising a film of a synthetic polymeric material having incorporated therein an amount of a first antiseptically active broad-spectrum antimicrobial agent, and a pressure sensitive adhesive coated onto one surface of said film, said pressure sensitive adhesive optionally having incorporated therethrough a second antiseptically active broad-spectrum antimicrobial agent. The first and second antimicrobial agents may be different or may be the same. The latter inventive surgical drape is able to provide timed release of the antimicrobial agents from both the drape material itself and the adhesive, which is used to attach the drape material to skin. The use of antimicrobial agents in both the drape material and the adhesive further reduces the risk of infection to a patient and to medical personnel working on the patient.

In yet another embodiment, the present invention relates to a sheet material for use as a surgical drape which releases an antiseptically active broad-spectrum antimicrobial agent when placed in contact with skin produced by a process comprising the steps of: providing a mixture of polymeric material and an antimicrobial agent in which said antimicrobial agent is uniformly dispersed in said polymeric material; and forming said mixture into a thin film. The formation of the thin film is preferably accomplished by utilizing an extrusion technique.

Accordingly, it is an object of the present invention to provide a surgical drape capable of reducing the risk of infection to a patient.

It is a further object of the present invention to provide a surgical drape capable of releasing an antiseptically active broad-spectrum antimicrobial agent to a patient when the drape is placed in contact with skin.

It is yet a further object of the present invention to provide an adhesive associated with a surgical drape wherein both the adhesive and the surgical drape are able to release an antiseptically active broad-spectrum antimicrobial agent when placed in contact with skin.

It is an additional object of the present invention to produce a surgical drape wherein the drape is produced by forming a film of a polymeric material having dispersed therein an antimicrobial agent.

These and other objects will be readily recognized and understood by one skilled in the art as reference is made to the following detailed description of the preferred embodiments.

DETAILED DESCRIPTION OF THE PREFERRED EMBODIMENTS

While describing the preferred embodiments, specific terminology will be utilized for the sake of clarity. It is to be understood that such terminology includes not only the recited embodiments, but all technical equivalents which perform substantially the same function in substantially the same way to obtain the same result.

The present invention is directed to surgical drapes generally and is particularly suited to drapes which employ polymeric substrates. The inventive surgical drape is applied to the patient at the portion of the body where a surgical incision is to be made. The surgical drape is characterized by having incorporated in its substrate material an antiseptically effective amount of a broad-spectrum antimicrobial agent. When used, the antimicrobial agent migrates to the outer surface of the substrate where it is released to the patient. Once present upon the skin, the agent acts to inhibit bacterial growth and promote asepsis. As the agent is removed by the skin, it is replenished from the drape.

The thin sheet substrate used as the surgical drape may be selected from a number of materials. The substrate may be a woven or knitted fabric comprised of antimicrobial containing fibers or a nonwoven fabric, but a plastic or polymeric film, e.g., polyvinyl chloride, polypropylene polyethylene or polyurethane, is particularly preferred. The polymeric films are continuous in that they have no openings, but the moisture vapor transmissive character of the films are based on the permeability of the materials to moisture vapor. These films are generally impermeable to liquid water and to other liquids. Examples of polymeric substrates useful in the present invention are described in U.S. Pat. No. 3,645,835 to Hodgson and are commercially available.

The substrate, preferably a polymeric sheet, can be up to 75 microns in thickness. More preferably it is less than 40 microns and usually about 30 microns in thickness.

Incorporated into and throughout the structure of the polymeric sheet is an antiseptically active broad-spectrum antimicrobial agent which releases from the polymeric sheet upon contact with human skin. The antimicrobial agent functions to prevent bacterial growth at the site of incision and further functions to provide protection to medical personnel working on the patient.

A large number of antimicrobial agents are contemplated for use in the present invention. Examples of such antimicrobial agents include:
  (i) metal salts, or like compounds with antibacterial metal ions, e.g., copper, mercury or silver, and optionally with additional nonmetallic ions of antibacterial properties;
  (ii) typical antibiotics, e.g., neomycin, soframycin, bacitracin, polymcin;
  (iii) antibacterials such as chlorhexidine and its salts;
  (iv) quaternary ammonium compounds, e.g., centrimide, domiphen bromide, and polymeric quaternaries;
  (v) iodophors such as povidone iodine, and polyvinylpyrrolidone-iodine (PVP-I);
  (vi) acridine compounds such as 9-aminoacridine,: 3,6-diaminoacridine and 6,9-diamino-2-ethoxyacridine;
  (vii) biguanidine compounds such as 1,6-di(4-chlorophenylbiguanido)hexane, diaminohexylbiguanide, 1,6-di(aminohexylbiguanido)hexane; and polyhexamethylenebiguanide.
  (viii) 5-chloro-2-(2,4-dichlorophenoxy)phenol available under the name Microban ® from Microban Products In the preferred embodiment, the antimicrobial agent of choice is 5-chloro-2-(2,4-dichlorophenoxy)phenol.

The antimicrobial agent is preferably present in the drape in an amount of about 0.01% to about 25% by weight of substrate material, more preferably between about 1 and about 5% by weight.

To produce the inventive surgical drapes, the polymeric material and the antimicrobial agent are mixed together to uniformly and stably disperse the antimicrobial agent in the polymeric material, and a sheet is mechanically formed by procedures known in the art. Examples of such procedures include solvent casting, film injection molding and extrusion techniques such as film blowing. In the preferred embodiment, a film blowing extrusion technique is used.

For example, when producing a polyethylene surgical drape having an antimicrobial dispersed therein by an extrusion technique, a blow film type extruder having a circular die is used to produce a drape having a thickness of less than 75 microns. This technique involves extrusion of polyethylene feed through the circular die, followed by expansion, cooling, and collapsing of the blown bubble. In operation, the blown film is extruded through guiding devices into a set of pinch rolls which flatten it. An example of such a blown film extruder is disclosed in U.S. Pat. No. RE 28,600.

In an embodiment wherein a fabric drape is produced, the antimicrobial agent is directly added to the fabric forming material such as the fiber from which the yearns and threads forming the fabric are formed. The resultant material is then formed into a drape by knitting, in the case of a knitted drape, or by utilizing process techniques known in the art to produce a nonwoven fabric.

To apply the surgical drape to the patient, it is necessary that an adhesive be provided. The adhesive may first be applied to the patient in an independent layer and the drape then applied to the patient by attachment to the adhesive, although this is generally undesirable. Preferably, the adhesive is a pressure-sensitive adhesive applied directly to the surgical drape and maintained in a non-adherent condition prior to use by the use of means known in the art, such as release papers. The adhesive is further selected to enable the passage of the antimicrobial agent from the drape material through the adhesive to release its antimicrobial properties upon contact with the patient's skin and preferably has a high moisture vapor permeability.

Adhesives which are preferred in the present invention are compatible with the antimicrobial agent and are generally water or solvent based dermatologically compatible pressure-sensitive adhesives. The adhesives may be made with hydrophobic polymers or with mixed hydrophobic and hydrophilic polymers. A preferred adhesive is an adhesive which exhibits some hydrophilic properties as evidenced by its ability to pick up water. The ability of the adhesive to pick up water may ensure that the moisture from the skin of the patient will assist the antimicrobial agent in migrating at or immediately below the surface of the adhesive to deliver the antimicrobial to the patient. Classes of pressure-sensitive adhesives include polyacrylates, polyolefins, silicone adhesives, polyvinyl ethers, polyesters, polyurethanes, etc. as well as selected copolymers thereof. The formulation of these adhesives is well known in the art, e.g. U.S. Pat. Nos. Re 24,906, 2,973,286, 3,307,544, 3,645,835, etc. It will be appreciated by one skilled in the art that the aforestated adhesive components might also include various chemical modifiers so as to enable them to have the utility desired, e.g., tackifiers, cross-linkers, stabilizers, initiators, etc.

As discussed above, polyvinyl ethyl ether adhesives may be used in connection with the present invention. These adhesives may be obtained in a wide range of viscosities. Particularly preferred adhesives are disclosed in U.S. Pat. No. 3,645,835.

A number of known polyacrylate adhesives may be used in the present invention. For example, polyhydroxy propyl acrylate is a tacky rubbery polymer which may be converted into a pressure-sensitive adhesive composition by copolymerization. The homopolymers generally cross-link during polymerization but linear polymers may be obtained by solvent polymerization provided the concentration of monomer is low.

Suitable acrylate ester copolymer adhesives include Acronal KR 2136 (B.A.S.F.) and D.260 (Shawinigan). Blends of acrylic and polyvinyl ethers found to be useful as adhesives include (a) a mixture of 50 parts by weight Acronal 40D (B.A.S.F.) and 50 parts by weight Lutanol M 40, and (b) a mixture of 100 parts by weight Gantrez M 574, 50 parts by weight Gelva D260 and 25 parts by weight of Kelrez ZR 142.

Other polyacrylate adhesives include polymers of 2-ethylhexylacrylate polymerized with a number of different other monomers. Typical of this type of adhesive is Gelva 788 available from Monsanto Chemical Company. Other similar adhesives are copolymers of an acrylate and styrene. These adhesives are hydrophobic in nature.

Typical of hydrophilic polymers are copolymers of isooctylacrylate and n-vinylpyrrolidone in a weight ratio of 85/15. The distinction between hydrophobic polymer and hydrophilic polymer is based on the ability of a sample of the polymer to absorb water in a 24 hour time period at room temperature.

It is additionally possible to incorporate an antimicrobial agent in the adhesive. Antimicrobial agents which may be incorporated into the adhesive include those from groups (i) - (viii) as described above. A particularly preferred antimicrobial agent is 5-chloro-2-(2,4-dichlorophenoxy)phenol. In the embodiment where the adhesive is directly applied to the inventive surgical drape, it is particularly preferred to use an adhesive having an antimicrobial agent dispersed therein to provide additional protection to the surgery patient.

To disperse the antimicrobial agent into the adhesive, techniques such as mixing the antimicrobial agent directly into the adhesive or solvent evaporation techniques such as those disclosed in U.S. Pat. Nos. 4,310,509 and 4,643,181 are used. Solvent evaporated techniques typically involve forming an emulsion of the antimicrobial agent in a solvent, and mixing the emulsion into the adhesive so that the antimicrobial agent is uniformly dispersed as a separate phase throughout the adhesive medium. The solvents used to form the emulsion may be a single type of solvent or a combination of solvents selected from water or water soluble solvents such as methanol, ethanol, ethyl acetate, tetrahydrofuran and the like. Mixing of the emulsion typically occurs at low mixing rates, about 300 rpm, and at ambient temperatures.

The antimicrobial agent is preferably present in an amount of about 0.1% to about 25% by weight of adhesive, more preferably about 1% to about 5% by weight. When using hydrophilic adhesives, amounts less than 1% may be used.

In the embodiment when the adhesive is directly applied to the surgical drape, the adhesive may be applied to the drape in solution as an aqueous dispersion, as a hot melt, or by a transfer process using known techniques such as knife, roller-coating or curtain-coating methods. The transfer process is particularly preferred.

In a transfer process, an adhesive emulsion including a water or a different solvent, optionally containing an antimicrobial agent, is spread onto a sheet of release paper and dried to remove the water or solvent. The inventive surgical drape is then brought into contact with the adhesive and calendered to insure that the adhesive adheres to the drape. The surgical drape will generally include a release sheet covering the adhesive and the release sheet on which the adhesive is deposited can be used for that purpose or that release sheet can be removed and replaced with another release sheet which is generally a silicone coated paper material. In the embodiment where the adhesive contains an antimicrobial agent, when the mixture of adhesive and antimicrobial agent is dried after coating on the release sheet, the antimicrobial agent remains dispersed in the adhesive.

In the embodiment where the adhesive layer is adhered to the outer surface of the drape material, the thickness of the adhesive layer is preferably between about 30 and 80 microns, and more preferably between 40 and 50 microns. The adhesive is coated on the drape at a coating level of approximately 30 to 70 grams per square meter to produce the coating thickness that is desired. The preferred coating level is about 50 to 65 grams per square meter.

The inventive surgical drape may also include additional materials to conform to the desired use, such as commercially available antistatic materials. An example of such an antistatic material is Electrosol S-1-X, manufactured by Alframine.

The invention is further illustrated by the following nonlimiting examples.

EXAMPLE 1

0.375 pounds of 5-chloro-2-(2,4-dichlorophenoxy) phenol is mixed with 7.125 pounds of polyethylene pellets to form a mixture. This mixture contains approximately 5% by weight 5-chloro-2-(2,4-dichlorophenoxy) phenol. The mixture is then added to an additional 28 pounds of polyethylene pellets, and is uniformly mixed. The resulting mixture is then extruded into a thin film having a thickness of about 35 microns by utilizing a blown film type extruder having a circular die. The film is then cut to a size suitable for use as a surgical drape and is applied to a patient's skin by use of an adhesive. When an incision is made into the surgical drape, the 5-chloro-2-(2,4-dichlorophenoxy)phenol dispersed in the polyethylene migrates outwardly to the surface of the drape to enable it to contact with the patient's skin.

EXAMPLE 2

To produce a drape including an adhesive bound to one of its external surfaces, 0.375 pounds of 5-chloro-2-(2,4-dichlorophenoxy)phenol is dispersed in 18.375 pounds of a water based acrylic adhesive. The resulting dispersion is spread onto a sheet of silicone type release paper and is dried in an oven to remove the water contained in the adhesive. The adhesive containing release sheet is then brought into contact with an external surface of the surgical drape of Example 1 and is passed through the nip between a pair of pressure rolls at 60 lbs./in.$^2$ to adhere the adhesive to the drape.

The surgical drapes of the present invention provide a number of advantages as set forth below:

1. They have the ability to release an antimicrobial agent to a surgical wound over a period of time to reduce the risk of infection.
2. They provide additional protection to medical personnel working on a patent.
3. They may be left in position on the body for extended periods of time which:
   a. enables the drape to be adhered over the proposed area of operation and the incision line to be marked on the drape during preoperative periods;
   b. enables the incision to be made accurately through the drape, the drape preventing wound infection from the surrounding area; and
   c. enables the incision to be closed by surface suture strips and, if necessary, covered by an adhesive dressing adhering to the surface of the drape to allow the whole assembly to be left in contact with the body surface until the incision is healed.

Having described the invention in detail and by reference to the preferred embodiments thereof, it will be apparent that modifications and variation are possible without departing from the scope of the appended claims.

What is claimed is:

1. A sheet material for use as a surgical drape comprising:
   a polyethylene film or fabric having external surfaces, said film or fabric having incorporated therethrough 5-chloro-2-(2,4-dichlorophenoxy)phenol in an amount of about 0.01% to about 25% by weight of said film; and
   a pressure sensitive adhesive coated into one of said external surfaces, said pressure sensitive adhesive having incorporated therethrough an amount of 5-chloro-2-(2,4-dichlorophenoxy)phenol in an amount of about 0.01% to about 25% by weight of said adhesive.

2. A flexible sheet material for use as a surgical drape comprising polyethylene film or fabric having incorporated therein 5-chloro-2-(2,4-dichlorophenoxy)phenol in an amount of about 0.01% to about 25% by weight of said film or fabric, said sheet further comprising an adhesive covering an exterior surface of said polyethylene film or fabric so that said sheet can be attached to a patient, said adhesive being selected from the group consisting of polyvinyl ethers, acrylic adhesives, polyolefins, silicone adhesives, polyesters, and polyurethanes.

3. The sheet material according to claim 2 wherein said adhesive further comprises 5-chloro-2-(2,4-dichlorophenoxy)phenol dispersed therein.

4. A flexible sheet material for use as a surgical drape which releases 5-chloro-2-(2,4-dichlorophenoxy)phenol when placed in contact with the skin of a patient produced by a process comprising the steps of:
   providing a polyethylene material;
   mixing 5-chloro-2-(2,4-dichlorophenoxy)phenol with said polyethylene material to form a mixture in which said 5-chloro-2-(2,4-dichlorophenoxy)phenol is uniformly dispersed in said polyethylene material in an amount of about 0.01 to about 25% by weight;
   forming said mixture into a thin film;
   providing a pressure-sensitive adhesive material selected from the group consisting of polyvinyl ethers, acrylic adhesives, olyolefins, silicone adhesives, polyesters, and polyurethanes; and
   applying said pressure-sensitive adhesive material to an external surface of said thin film wherein said step of providing a said pressure-sensitive adhesive material and said step of applying said pressure-sensitive material occurs after said step of forming said mixture into said film.

5. The sheet material according to claim 4 wherein said pressure sensitive adhesive material further comprises 5-chloro-2-(2,4-dichlorophenoxy)phenol dispersed therein.

* * * * *